United States Patent
Daniels

(10) Patent No.: US 8,901,034 B2
(45) Date of Patent: Dec. 2, 2014

(54) METHOD OF IMPROVING PLANT GROWTH BY SEED TREATMENT

(75) Inventor: Jeffrey Daniels, W. Des Moines, IA (US)

(73) Assignee: Bayer CropScience LP, Research Triangle Park, NC (US)

( * ) Notice: Subject to any disclaimer, the term of this patent is extended or adjusted under 35 U.S.C. 154(b) by 242 days.

(21) Appl. No.: 13/130,650

(22) PCT Filed: Nov. 30, 2009

(86) PCT No.: PCT/US2009/066070
§ 371 (c)(1),
(2), (4) Date: Jul. 13, 2011

(87) PCT Pub. No.: WO2010/071735
PCT Pub. Date: Jun. 24, 2010

(65) Prior Publication Data
US 2011/0263420 A1    Oct. 27, 2011

Related U.S. Application Data

(60) Provisional application No. 61/203,165, filed on Dec. 19, 2008.

(51) Int. Cl.
| | | |
|---|---|---|
| *A01C 1/06* | (2006.01) | |
| *A01N 43/80* | (2006.01) | |
| *A01N 51/00* | (2006.01) | |
| *A01N 37/46* | (2006.01) | |
| *A01N 53/00* | (2006.01) | |
| *A01N 47/26* | (2006.01) | |

(52) U.S. Cl.
CPC ............... *A01N 51/00* (2013.01); *A01N 37/46* (2013.01); *A01N 53/00* (2013.01); *A01C 1/06* (2013.01); *A01N 47/26* (2013.01)

USPC .................. 504/100; 504/103; 504/271

(58) Field of Classification Search
CPC ... A01N 53/00; A01N 51/00; A01N 2300/00; A01N 43/80; A01N 47/26; A01N 37/46; A01C 1/06
USPC ......................... 504/100, 103, 271
See application file for complete search history.

(56) References Cited

U.S. PATENT DOCUMENTS

| | | |
|---|---|---|
| 2005/0267053 A1 | 12/2005 | Hofer et al. |
| 2006/0029576 A1 | 2/2006 | Huang et al. |
| 2007/0092547 A1 | 4/2007 | Birnbaum et al. |
| 2007/0135506 A1 | 6/2007 | Zuen et al. |

FOREIGN PATENT DOCUMENTS

| | | |
|---|---|---|
| WO | WO 2008037489 A2 * | 4/2008 |
| WO | 2008107097 | 9/2008 |
| WO | WO 2008107097 A1 * | 9/2008 |

OTHER PUBLICATIONS

International Search Report for PCT/US2009/066070, Dec. 19, 2008.

* cited by examiner

*Primary Examiner* — Johann R Richter
*Assistant Examiner* — Courtney Brown

(57) ABSTRACT

A method of improving the growth of a plant is provided, comprising the steps of applying an effective amount of a base treatment composition and an effective amount of a second treatment composition to seeds prior to planting, either simultaneously or separately in succession. The base treatment composition comprises at least one fungicide that is different from hymexazol and the second treatment composition comprises a first component comprising a neonicotinoid such as clothianidin and, optionally, but preferably, a synthetic pyrethroid such as beta-cyfluthrin, and a second component comprising hymexazol as at least one of its active ingredients.

32 Claims, No Drawings

METHOD OF IMPROVING PLANT GROWTH BY SEED TREATMENT

FIELD OF THE INVENTION

The present invention is directed to methods of improving plant growth by treating seeds with a novel seed treatment.

BACKGROUND OF THE INVENTION

The United States ranks among the top four sugar producers in the world. Sugarbeet is a major player in this industry.

Sugarbeet seed routinely receives a treatment of fungicide prior to planting. Traditionally, these fungicide applications are designed to protect against seed-borne or early season diseases attacking the seed or seedling.

In terms of specific fungicides, many compounds are currently known to function as seed treatment based fungicides. One compound of particular interest to the present application is 3-hydroxy-s-methyl isoamyl-azol represented by the chemical formula:

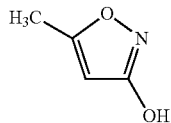

and is commonly known as hymexazol. Sankyo Agro Company Limited of Tokyo, Japan obtained United States Trademark Registration 1,366,137 (which currently stands cancelled) to sell fungicides, pursuant to which it marketed and sold hymexazol under the mark "Tachigaren". Since at least the mid 1980's, in the United States, hymexazol has been applied to at least a portion of the treated sugarbeet seeds to protect against disease caused by *Aphanomyces*.

To those skilled in the sugarbeet seeds art, the terms "pelleted" and "minimum" when referring to seed coatings each have a commonly understood meaning. A "pelleted" coated sugarbeet seed has a weight gain of coatings placed on the seed of greater than 200% of the uncoated seed's original weight.

A "minimum" (also known as "a minimum build-up") coated sugarbeet seed has a weight gain of coatings placed on the seed of between about 30% to about 200% of the uncoated seed's original weight.

It was commonly accepted by those skilled in the art that application of the higher labeled rates of hymexazol could be placed only on pelleted seed because it had been observed that applying higher labeled rates of hymexazol to seeds with minimal weight build-up undesirably contributed to poor germination and decreased field emergence of the seedlings of the sugarbeet crop when compared to similar controls not treated with hymexazol.

It was accepted by those skilled in the art that only by placing said higher rates of hymexazol near the outside perimeter of pelleted seed would the probability of observing the undesirable decreased field emergence associated with the hymexazol when applied at said higher rates be lowered or eliminated because the coating material was needed to form a barrier between the hymexazol and the seed to prevent hymexazol from harming the seed. In terms of what might constitute a "higher" or a "lower" rate of application of hymexazol, those skilled in the art will appreciate that hymexazol is currently generally used at one of two application rates: a "lower" use rate of 20 grams active ingredient per 100,000 seeds (commonly marketed under the mark "Tachigaren 20" by Sankyo Agro Chemical Company) or a "higher" use rate of 45 grams active ingredient per 100,000 seeds (commonly marketed under the mark "Tachigaren 45" by Sankyo Agro Chemical Company). The lower use rate (e.g. Tachigaren 20), in recent years, has been applied to seeds with minimum build-up (meaning as noted above, between about 30% and about 200 percent weight gain build-up). It is currently understood by those skilled in the art that the higher application rate (e.g. Tachigaren 45) must still be applied only to pelleted sugarbeet seeds due to concerns related to poorer field emergence.

And it should be noted that it is desirable in most applications to use sugarbeet seed treated with higher rates of hymexazol in fields with a history of high incidence of disease caused by *Aphanomyces* or similar diseases. And it is further desired where possible to plant minimum build-up seed versus pelleted seed because pelleted seed is generally more expensive to purchase, due in part to the extra time and materials needed to provide the additional coating thickness. Thus, using higher rates of hymexazol with minimum build-up seed has long been highly desired by those growing sugarbeet crops, and would have been a preferred course of action if it were not for the problem of poorer field emergence.

It would be desirable to develop an effective chemical seed treatment method for the improvement of plant growth, taking advantage of the benefits derived from each of the above-mentioned agricultural chemicals, without the known detrimental effects. An effective chemical treatment would improve plant growth through increased emergence. In particular it would be desirable to be able to apply the higher application rates of hymexazol to sugarbeet seeds, whether having pelleted or minimal coatings, and yet still avoid having lowered field emergence.

SUMMARY OF THE INVENTION

A method of improving the growth of a plant is provided. By "improving the growth of a plant" is meant that an increased number of plant emergences is observed in seeds that have been treated in accordance with the method of the present invention, compared to seeds that have not been so treated. The method comprises the steps of applying a base treatment composition and a second treatment composition to seeds prior to planting, either simultaneously or separately. The base treatment composition comprises at least one fungicide that is different from hymexazol. The second treatment composition comprises a first component and a second component. The first component is a neonicotinoid such as but not limited to clothianidin, and further optionally, but preferably, includes a synthetic pyrethroid such as but not limited to beta-cyfluthrin. The second component comprises hymexazol.

DETAILED DESCRIPTION OF THE INVENTION

Other than in the operating examples, or where otherwise indicated, all numbers expressing quantities of ingredients, reaction conditions and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa; e.g., the singular forms "a," "an," and "the" include plural referents unless expressly and unequivocally limited to one referent.

With respect to the present invention, the phrase "effective amount" as used herein is intended to refer to an amount of an ingredient used such that a noticeable increase in number of plant emergences is observed in plants grown from seeds treated using the method of the present invention, compared to seeds that did not receive such treatment.

The method of the present invention comprises the steps of applying a base treatment composition and a second treatment composition to seeds prior to planting, either simultaneously or separately; for example, the base treatment composition may be applied prior to and separately from the second treatment composition. In an alternative embodiment of the present invention, instead of applying a base treatment composition and a second treatment composition, all components of both the base and second treatment compositions may be mixed together and applied as a single treatment composition. The base treatment composition comprises an effective amount of at least one fungicide that is different from hymexazol and the second treatment composition comprises an effective amount of a first component comprising a neonicotinoid such as but not limited to clothianidin and, optionally but preferably, a synthetic pyrethroid such as but not limited to beta-cyfluthrin, and an effective amount of a second component comprising hymexazol.

Seeds that can be treated using the present method include but are not limited to beet seeds, such as sugarbeet and fodder beet. As is typical in the industry, sugarbeet seeds are supplied to growers after being coated with inert materials ("weight build up") to improve consistency in size and shape, and also to allow incorporation and layering of agricultural chemicals such as pesticides, in many cases, without direct contact with the seed. The seeds to be treated in accordance with the method of the present invention may be pelleted seeds (also known as seed pellets); i.e., seeds that have a weight build up of greater than 200% due to the layering of inert materials as described in more detail above. Alternatively the seeds to be treated in accordance with the method of the present invention are seeds that have a minimum weight build up; i.e., a weight gain of only 30 to 200% as described in more detail above. The hymexazol may be applied at rates of about 20 grams active ingredient per 100,000 seeds or more and may even be applied at rates of about 45 grams active ingredient per 100,000 seeds or more to either pelleted or minimum build-up seeds. This is very clearly an unexpected advantage of the method of the present invention because heretofore it was observed and believed and accepted by those skilled in the art that hymexazol could not be applied to seeds that were not pelleted at these higher rates without detrimentally affecting germination and emergence of plants as explained above.

The compositions may be applied to seeds by any known method, but are typically applied by spraying and tumbling.

The base treatment composition comprises at least one fungicide that is different from hymexazol. Suitable fungicides within the scope of the present invention include those identified in the Fungicide Resistance Action Committee ("FRAC") Code List (Last Update December 2006) which is hereby incorporated herein in its entirety by reference. Particular fungicides include triazoles, including azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, Tebuconazole, tetraconazole, triadimefon, triadimenol, triticonazole and combinations thereof. Other fungicides that may be included within the scope of the present invention include isotianil, fluopicolide, 2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-s; bromuconazole; bupirimate; buthiobate; butylamine; calcium polysulfide; capsimycin; captafol; captan; carbendazim; carboxin; carpropamid; carvone; chinomethionate; chlobenthiazone; chlorfenazole; chloroneb; chlorothalonil; chlozolinate; clozylacon; cyazofamide; cyflufenamide; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-m; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-al; fosetyl-sodium; fuberidazole; furalaxyl; furametpyr; furcarbanil; furmecyclox; guazatine; hexachlorobenzene; hexaconazole; imazalil; imibencronazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoximmethyl; mancozeb; maneb; meferimzone; mefenoxam; mepanipyrim; mepronil; metalaxyl (N-(2,6-dimethylphenyl)-N-(methoxyacetyl)alanine methyl ester); metalaxyl-m; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; pyraclostrobin; pyrazophos;

pyrifenox; pyrimethanil; pyroquilon; pyroxyfur; pyrrolnitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram (tetramethylthiuram disulfide); tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin a; vinclozolin; zineb; ziram; zoxamide; (2S)-N-[2-[4-[[3-(4-chlorophenyl)-2-propinyl]oxy]-3-methoxyphenyl]ethyl]-3-methyl-2-[(methylsulfonyl)amino]-butanamide; 1-(1-naphthalenyl)-1H-pyrrol-2,5-dione; 2,3,5,6-tetrachloro-4-(methylsulfonyl)-pyridine; 2-amino-4-methyl-n-phenyl-5-thiazolcarboxamide; 2-chloro-N-(2,3-dihydro-1,1,3-trimethyl-1H-inden-4-yl)-3-pyridincarboxami-de; 3,4,5-trichloro-2,6-pyridindicarbonitrile; actinovate; cis-1-(4-chlorophenyl)-2-(1H-1,2,4-triazol-1-yl)-cycloheptanol; methyl-1-(2,3-dihydro-2,2-dimethyl-1H-inden-1-yl)-1-Himidazol-5-carboxyla-te; monopotassium carbonate; n-(6-methoxy-3-pyridinyl)-cyclopropancarboxamide; n-butyl-8-(1,1-dimethylethyl)-1-oxaspiro[4.5]decan-3-amine; sodium trathiocarbonate; and copper salts and preparations, such as: Bordeaux mixture, copper hydroxide, copper naphthenate, copper oxychloride, copper sulphate, cufraneb, copper oxide, mancopper, oxine-copper, and combinations thereof. In certain embodiments, the base treatment composition comprises a combination of fludioxonil and mefenoxam, (commercially available from Syngenta Corporation of Wilmington, Del. as "MAXIM 4FS" and "APRON XL", respectively.) Often the base treatment composition may comprise tetramethylthiuram disulfide (commonly known as "thiram") and/or N-(2,6-dimethylphenyl)-N-(methoxyacetyl)alanine methyl ester (commonly known as "metalaxyl"). Thiram is commercially available from Bayer CropScience LP of Research Triangle Park under the mark "42-S Thiram" and metalaxyl is commercially available also from Bayer CropScience LP under the mark "ALLEGIANCE", respectively.)

In certain embodiments of the present invention, the base treatment composition further comprises one or more additional ingredients including but not limited to one or more safeners and/or pesticides, herbicides and/or additional fungicides. Pesticides include but are not limited to insecticides, acaracides, nematacides and combinations thereof. In particular, acibenzolar-S-methyl, phorate, aldicarb, chlorothalonil, acephate, tebuconazole, and/or neonicotinoids such as imidacloprid, thiacloprid, acetamiprid, clothianidin, nitenpyram, and thiamethoxam are suitable for use as additional ingredients in the primary treatment composition. Each of these is available commercially and may be used in the method of the present invention in amounts conventionally recommended for their intended use. In addition to the foregoing, the base treatment composition may include other components including but not limited to dyes, extenders, surfactants, defoamers and combinations thereof.

The second step of the method of the present invention is applying a second treatment composition to seeds prior to planting. As noted above, the second step may be performed simultaneously with the application of the base treatment composition, or after and separately from the application of the base treatment composition. The second treatment composition comprises effective amounts of:
  (a) a first component comprising a neonicotinoid such as but not limited to clothianidin and, optionally but preferably, a synthetic pyrethroid such as but not limited to beta-cyfluthrin; and
  (b) a second component comprising hymexazol.

The two components of the second treatment composition may be applied simultaneously together or separately in succession in any order to the seeds.

The neonicotinoids of the first component within the scope of the present invention include, but are not limited to, imidacloprid, thiacloprid, acetamiprid, clothianidin, nitenpyram, thiamethoxam and combinations thereof.

In one embodiment of the present invention, the first component (a) is preferably a mixture of clothianidin and beta-cyfluthrin. Such a combination of the insecticides clothianidin plus beta-cyfluthrin has received federal registration from the United States Environmental Protection Agency ("EPA") for use and sale, for among other purposes, as a seed treatment application to sugarbeet seed in March of 2008, and in accordance with that registration, Bayer CropScience LP of Research Triangle Park, N.C. markets a product under the mark "Poncho Beta". The Poncho Beta product is a mixture of 34.3% clothianidin and 4.5% beta-cyfluthrin in an aqueous medium which is labeled to be applied at a rate of 68 grams active ingredients per 100,000 seeds (the 68 grams of active ingredients comprises 60 grams of clothianidin plus 8 grams of beta-cyfluthrin). The Poncho Beta product is designed to protect against early season insect damage caused by seed and seedling attacking insects.

The second component (b), hymexazol may be applied to seeds in an application rate of at least about 20, and, optionally, still higher at a rate of at least about 45 grams or more of active ingredient per 100,000 seeds, regardless of whether the seeds are pelleted or have a minimum build-up coating.

Either or both components of the second treatment composition can include one or more additional ingredients including but not limited to safeners, pesticides, herbicides, additional fungicides and combinations thereof. Pesticides can include but are not limited to one or more of insecticides, acaracides, nematacides, and combinations thereof. Particular mention is made of one or more of the neonicotinoids as disclosed above, aldicarb, phorate, acephate, acibenzolar-S-methyl, chlorothalonil, tebuconazole, and/or any other known pesticides as used in the art. In addition, either or both components of the second treatment composition may include other components including but not limited to dyes, extenders, surfactants, defoamers and combinations thereof.

Each of the treatment compositions used in the method of the present invention may independently be provided in common forms known in the art, for example as emulsifiable concentrates, suspension concentrates, directly sprayable or dilutable solutions, coatable pastes, dilute emulsions, wettable powders, soluble powders, dispersible powders, dusts, granules or capsules. They may each optionally include auxiliary agents commonly used in agricultural treatment formulations and known to those skilled in the art. Examples include but are not limited to wetting agents, dispersants, emulsifiers, penetrants, preservatives, antifreezes and evaporation inhibitors such as glycerol and ethylene or propylene glycol, sorbitol, sodium lactate, fillers, carriers, colorants including pigments and/or dyes, pH modifiers (buffers, acids, and bases), salts such as calcium, magnesium, ammonium, potassium, sodium, and/or iron chlorides, fertilizers such as ammonium sulfate and ammonium nitrate, urea, and defoamers.

Suitable defoamers include all customary defoamers including silicone-based and those based upon perfluoroalkyl phosphinic and phosphonic acids, in particular silicone-based defoamers, such as silicone oils, for example.

Defoamers most commonly used are those from the group of linear polydimethylsiloxanes having an average dynamic viscosity, measured at 25° C., in the range from 1000 to 8000 mPas (mPas=millipascal-second), usually 1200 to 6000 mPas, and containing silica. Silica includes polysilicic acids, meta-silicic acid, ortho-silicic acid, silica gel, silicic acid gels, kieselguhr, precipitated $SiO_2$, and the like.

Defoamers from the group of linear polydimethylsiloxanes contain as their chemical backbone a compound of the formula HO—[Si($CH_3$)$_2$—O—]$_n$—H, in which the end groups are modified, by etherification for example, or are attached to the groups —Si($CH_3$)$_3$. Non-limiting examples of defoamers of this kind are RHODORSIL® Antifoam 416 (Rhodia) and RHODORSIL® Antifoam 481 (Rhodia). Other suitable defoamers are RHODORSIL® 1824, ANTIMUSSOL 4459-2 (Clariant), Defoamer V 4459 (Clariant), SE Visk and AS EM SE 39 (Wacker). The silicone oils can also be used in the form of emulsions.

The present invention will further be described by reference to the following examples. The examples are merely illustrative of the invention and are not intended to be limiting. Unless otherwise indicated, all parts are by weight.

EXAMPLES

The following examples (3 and 4) illustrate the treatment of seeds using the method of the present invention, demonstrating combinations of treatment compositions on different seeds and their combined effects on plant growth. Examples 1, 2, 5, and 6 are comparative.

Sugarbeet seed was secured for an in-field research trial. Three seed sources were obtained with differing levels of strength of emergence. These can be described as strong emerging, weak emerging, and strong emerging but poorer germination. All three of these seed sources could be classified as "ROUNDUP Ready" (Monsanto) for their tolerance to glyfosate, although the present invention certainly is not limited to only "ROUND-UReady" sugarbeet seeds, and any sugarbeet seeds, whether "ROUND-UReady" or not are contemplated as within the scope of the present invention.

The application of both weight gain build-up and seed treatment chemical was conducted by BetaSeed, Inc., of Tangent, Oreg. Two levels of weight gain build-up were utilized. These can be described as "PRO50", (a branded application rate by BetaSeed, Inc.), having approximately 50 percent weight gain, and "4M Pellet", (also a branded application rate by BetaSeed Inc.), wherein "4M" refers to the 4 millimeter nominal size of the seed after application of the build-up coating, which are pelleted seeds having at least 200 percent weight gain.

The following chemical seed treatment products were applied in the various combinations set forth below in accordance with their authorized label rates to these BetaSeed Inc., PRO50 and 4M Pellet coated sugarbeet seeds for a total of six treatment types as follows:
1. Base=tetramethylthiuram disulfide (available as the 42-S Thiram product from Bayer CropScience LP) and metalaxyl (available as the ALLEGIANCE product, also from Bayer Crop Science LP),
2. Base+clothianidin and beta cyfluthrin (available in combination as the PONCHO Beta product from Bayer Crop Science LP), (a mixture of 34.3% clothianidin and 4.5% beta-cyfluthrin in an aqueous medium which is labeled to be applied at a rate of 68 grams active ingredients per 100,000 seeds (the 68 grams of active ingredients comprises 60 grams of clothianidin plus 8 grams of beta-cyfluthrin),
3. Base+the PONCHO Beta product+hymexazol (available as Tachigaren 20 from Sankyo Agro Company, LTD), (20 grams active ingredient per 100,000 seeds),
4. Base+PONCHO Beta product+hymexazol (available as Tachigaren 45 from Sankyo Agro Company, LTD), (45 grams active ingredient per 100,000 seeds),
5. Base+the Tachigaren 20 product, and
6. Base+the Tachigaren 45 product.

When combining seed source (3 sources), level of build-up (2 levels), and seed treatment types (6), a total of thirty six treatments were evaluated.

Two packets of fifty (counted) seeds were used to plant each plot. Each seed source was planted in a block to allow for easier viewing. Treatments were replicated six times and laid out in a six treatment by six replication Latin square design.

Planting date was also considered to be important. The field trial was planted at the Bayer Crop Science Field Technology Station near Sabin, Minn., on 5 May, an early planting date for sugarbeets in this geography. The trial was planted again on 15 May, a more normal planting date in this area.

Emerged plants were counted and recorded twice for each planting date. Plant stands were collected on 19 May and again on 28 May for the early planting date. Counts were made on 29 May and 10 June for the later plated trial. Numbers taken from each of the two row plot were combined to allow for a percent emergence (100 total seeds planted in each plot). The data was entered into and analyzed with Agronomy Research Manager ("ARM") computer software available from Gylling Data Management, Inc. Treatment differences were determined by using least significant difference (LSD=P.10).

Results

For both planting dates, the strong emerging seed source produced the greatest number of emerged plants. The seed source designated as poor germination produced the fewest number of plants.

When averaged across all seed sources, for the 5 May planting date, there was a significant difference among treatments for the minimum build-up seed. This was not true for pelleted seed. For minimum build-up (Table 2), each treatment which contained clothianidin plus beta-cyfluthrin (60.1%, 62.3%, 62.9%) produced significantly more plants than the base treatment (56.2%). Each of the hymexazol-alone treatments (57.7%, 57.7%) did not yield more plants than the base treatment. The combination of clothianidin plus beta-cyfluthrin and hymexazol produced significantly more plants than hymexazol by itself. This was true for both the 20 gram/100,000 seeds and the 45 gram/100,000 seeds application rates of hymexazol.

Seed Source

TABLE 1

Percent final field emergence for pelleted sugarbeet seed planted on 5 May.

| Treatment | Weak Emerging | Strong Emerging | Poor Germ | Average |
|---|---|---|---|---|
| Thiram/ALLEGIANCE (Base) | 62.3 | 66.3 | 49.7 | 59.4 |
| Base + PONCHO Beta (PB) | 62 | 71.3 | 47.8 | 60.4 |
| Base + PB + Tach 20 | 59 | 67.8 | 50.7 | 59.2 |
| Base + PB + Tach 45 | 63.3 | 73.8 | 49.5 | 62.2 |
| Base + Tachigaren 20 | 65.7 | 70.3 | 50.3 | 62.1 |

TABLE 1-continued

Percent final field emergence for pelleted
sugarbeet seed planted on 5 May.

| Treatment | Weak Emerging | Strong Emerging | Poor Germ | Average |
|---|---|---|---|---|
| Base + Tachigaren 45 | 61.3 | 69.2 | 45.8 | 58.8 |
| LSD P = .10 | 7.6 | 6.5 | 4.0 | 3.4 |

Seed Source

TABLE 2

Percent final field emergence for minimum build-up
sugarbeet seed planted on 5 May.

| Treatment | Weak Emerging | Strong Emerging | Poor Germ | Average |
|---|---|---|---|---|
| Thiram/ALLEGIANCE (Base) | 57.7 | 63.3 | 47.7 | 56.2 |
| Base + PONCHO Beta (PB) | 60.3 | 68.2 | 51.8 | 60.1 |
| Base + PB +Tach 20 | 61.0 | 71.2 | 54.8 | 62.3 |
| Base + PB +Tach 45 | 63.7 | 70.5 | 54.5 | 62.9 |
| Base + Tachigaren 20 | 57.8 | 64.7 | 50.5 | 57.7 |
| Base + Tachigaren 45 | 59.8 | 64.7 | 48.5 | 57.7 |
| LSD P = .10 | 6.7 | 6.4 | 5.0 | 3.2 |

Generally, emergence was greater for the 15 May planting date when compared to 5 May, indicating less planting time environmental stress. Again, the seed source designated as strong emerging produced the greatest number of plants. Averaged across seed sources, there were no significant differences among treatments for pelleted seed (Table 3).

Seed Source

TABLE 3

Percent final field emergence for pelleted sugarbeet
seed planted on 15 May.

| Treatment | Weak Emerging | Strong Emerging | Poor Germ | Average |
|---|---|---|---|---|
| Thiram/ALLEGIANCE (Base) | 59.7 | 72.0 | 54.8 | 62.2 |
| Base + PONCHO Beta (PB) | 58.0 | 83.8 | 51.7 | 64.5 |
| Base + PB + Tach 20 | 60.8 | 73.8 | 49.2 | 61.3 |
| Base + PB + Tach 45 | 61.3 | 73.8 | 50.5 | 61.9 |
| Base + Tachigaren 20 | 65.0 | 73.0 | 55.5 | 64.5 |
| Base + Tachigaren 45 | 58.0 | 78.3 | 48.2 | 61.5 |
| LSD P = .10 | 10.8 | 8.8 | 5.5 | 5.9 |

Once again for the minimum build-up seed source, when averaged across seed sources, significant treatment differences were recorded (Table 4). Only the combination of active ingredients clothianidin plus beta-cyfluthrin (as PONCHO Beta) by itself (66.3%) produced significantly more plants than the base treatment (61.7%). Each of the Tachigaren-alone treatments (59.4%, 59.8%) trended towards the fewest number of plants. Clothianidin plus beta-cyfluthrin, combined with each rate of Tachigaren (64.7%, 63.7%), produced more plants than Tachigaren alone.

Seed Source

TABLE 4

Percent final field emergence for minimum build-up sugarbeet
seed planted on 15 May.

| Treatment | Weak Emerging | Strong Emerging | Poor Germ | Average |
|---|---|---|---|---|
| Thiram/ALLEGIANCE (Base) | 58.0 | 67.7 | 59.3 | 61.7 |
| Base + PONCHO Beta (PB) | 64.8 | 77.5 | 56.5 | 66.3 |
| Base + PB + Tach 20 | 69.8 | 69.5 | 54.7 | 64.7 |
| Base + PB + Tach 45 | 64.7 | 70.0 | 56.3 | 63.7 |
| Base + Tachigaren 20 | 60.7 | 63.7 | 54.0 | 59.4 |
| Base + Tachigaren 45 | 58.5 | 66.0 | 54.8 | 59.8 |
| LSD P = .10 | 8.9 | 5.6 | 6.2 | 3.2 |

No early season disease symptoms or insect damage was observed or quantified in this trial. Measurable differences in stand counts are thought to be related to the products affect on seed safety and emergence.

Tachigaren did not produce higher stand counts when compared to the base treatment of Thiram and metalaxyl (ALLEGIANCE). It was expected that the combination of clothianidin plus beta-cyfluthrin and Tachigaren may have resulted in equal to or lower emergence than Tachigaren alone. Unexpectedly, the stand counts collected from this trial support that the combination of active ingredients clothianidin plus beta-cyfluthrin and Tachigaren resulted in higher emergence than the Tachigaren alone.

Tachigaren, at higher rates, may only be used on pelleted seed. However, these data of the present Examples support that minimum build-up may also be an option, when a neonicotinoid, such as clothianidin plus, optionally, but preferably, a synthetic pyrethroid such as beta-cyfluthrin is also applied.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of improving the growth of a beet plant, comprising the steps of:
    (i) applying an effective amount of a base treatment composition to beet seeds having minimum weight buildup prior to planting, wherein the base treatment composition comprises at least one fungicide that is different from hymexazol, wherein the at least one fungicide is selected from the group consisting of tetramethylthiuram disulfide, N-(2,6-dimethylphenyl)-N-(methoxyacetyl)alanine methyl ester, fludioxonil, and mefenoxam; and
    (ii) applying an effective amount of a second treatment composition to beet seeds having minimum weight buildup prior to planting, wherein the second treatment composition comprises:
        (a) a first component comprising a neonicotinoid and a synthetic pyrethroid, wherein the neonicotinoid is clothianidin and the synthetic pyrethroid is beta cyfluthrin; and (b) a second component comprising hymexazol as at least one active ingredient.

2. The method of claim 1, wherein the plant comprises sugarbeet.

3. The method of claim 1, wherein the base treatment composition is applied to the seeds prior to and separately from the second treatment composition.

4. The method of claim 1, wherein the base treatment composition and the second treatment composition are both applied to the seeds simultaneously.

5. The method of claim 1, wherein the first component (a) of the second treatment composition is applied to the seeds prior to and separately from the second component (b).

6. The method of claim 1, wherein the first component (a) of the second treatment composition is applied to the seeds after and separately from the second component (b).

7. The method of claim 1, wherein the first and second components of the second treatment composition are applied to the seeds simultaneously.

8. The method of claim 1, wherein all components of both the base treatment composition and second treatment composition are mixed with one another and applied as a single treatment composition.

9. The method of claim 1, wherein the second treatment composition further comprises other safeners, pesticides, herbicides, and/or fungicides.

10. The method of claim 1 wherein the base and/or second treatment composition further comprises dyes, extenders, surfactants, and/or defoamers.

11. The method of claim 1, wherein the base treatment composition comprises a combination of tetramethylthiuram disulfide and N-(2,6-dimethylphenyl)-N-(methoxyacetyl) alanine methyl ester.

12. The method of claim 1, wherein the base treatment composition comprises a combination of fludioxonil and mefenoxam.

13. The method of claim 1, wherein the first component (a) of the second treatment composition is applied in an amount of 68 grams of active ingredients/100,000 seeds.

14. The method of claim 1, wherein the second component (b) of the second treatment composition is applied at a rate of at least about 20 grams of active ingredient/100,000 seeds.

15. The method of claim 1, wherein the second component (b) of the second treatment composition is applied at a rate of at least about 45 grams of active ingredient/100,000 seeds.

16. A beet seed having minimum weight buildup having applied thereon:
   a) a composition comprising an effective amount of at least one fungicide that is different from hymexazol, wherein the at least one fungicide is selected from the group consisting of tetramethylthiuram disulfide, N-(2,6-dimethylphenyl)-N-(methoxyacetyl)alanine methyl ester, fludioxonil, and mefenoxam; and
   b) a composition comprising an effective amount of:
      (i) a first component comprising a neonicotinoid and a synthetic pyrethroid, wherein the neonicotinoid is clothianidin and the synthetic pyrethroid is beta cyfluthrin; and
      (ii) a second component comprising hymexazol as at least one active ingredient.

17. The seed of claim 16, wherein the seed is sugarbeet seed.

18. The seed of claim 16, wherein the composition of (a) is applied to the seeds prior to and separately from the composition of (b).

19. The seed of claim 16, wherein the composition of (b) is applied to the seeds prior to and separately from the composition of (a).

20. The seed of claim 16, wherein the composition of (a) and the composition of (b) are both applied to the seed simultaneously.

21. The seed of claim 16, wherein the composition of (b)(i) is applied to the seeds prior to and separately from the composition of (b)(ii).

22. The seed of claim 16, wherein the composition of (b)(i) is applied to the seeds after and separately from the composition of (b)(ii).

23. The seed of claim 16, wherein the first and second components of (b) are applied to the seeds simultaneously.

24. The seed of claim 16, wherein all components of the compositions of (a) and (b) are mixed with one another and applied as a single treatment composition.

25. The seed of claim 16, wherein the composition of (b) further comprises other safeners, pesticides, herbicides, and/or fungicides.

26. The seed of claim 16 wherein the composition of (a) and/or (b) further comprises dyes, extenders, surfactants, and/or defoamers.

27. The seed of claim 16, wherein the composition of (a) comprises a combination of tetramethylthiuram disulfide and N-(2,6-dimethylphenyl)-N-(methoxyacetyl)alanine methyl ester.

28. The seed of claim 16, wherein the composition of (a) comprises a combination of fludioxonil and mefenoxam.

29. The seed of claim 16, wherein the composition of (b)(i) is applied in an amount of 68 grams of active ingredients/100,000 seeds.

30. The seed of claim 16, wherein the composition of (b)(ii) is applied at a rate of at least about 20 grams of active ingredient/100,000 seeds.

31. The seed of claim 16, wherein the wherein the composition of (b)(ii) is applied at a rate of at least about 45 grams of active ingredient/100,000 seeds.

32. The method of claim 1, wherein the plant comprises sugarbeet or fodder beet.

* * * * *